United States Patent [19]

Graczyk et al.

[11] Patent Number: 5,451,599

[45] Date of Patent: Sep. 19, 1995

[54] COMPLEX SALTS OF HEMATOPORPHYRIN AND OF ITS DERIVATIVES, THEIR SYNTHESIS, AND THERAPEUTIC AGENT

[75] Inventors: Alfreda Graczyk; Jerzy Konarski, both of Warsaw, Poland

[73] Assignee: Wojskowa Akademia Techniczna im. Jaroslawa Dabrowskiego, Warsaw, Poland

[21] Appl. No.: 968,434

[22] Filed: Oct. 29, 1992

[30] Foreign Application Priority Data

Oct. 29, 1991 [PL] Poland ................................. 292220

[51] Int. Cl.$^6$ ..................... A61K 31/40; C07D 487/22
[52] U.S. Cl. ..................... 514/410; 514/397; 540/145
[58] Field of Search ................. 540/145; 514/397, 410

[56] References Cited

U.S. PATENT DOCUMENTS

| | | | |
|---|---|---|---|
| 4,849,207 | 7/1989 | Sakata et al. | 540/145 |
| 4,882,234 | 11/1989 | Lai | 514/185 |
| 4,961,920 | 10/1990 | Ward | 540/145 |
| 4,968,715 | 11/1990 | Dougherty et al. | 540/145 |
| 4,996,312 | 2/1991 | Sakata et al. | 540/145 |
| 5,190,966 | 3/1993 | Dougherty et al. | 540/145 |

FOREIGN PATENT DOCUMENTS 2912 11/1964 France .
9000392 1/1990 WIPO .
9006314 6/1990 WIPO .

OTHER PUBLICATIONS

Rimington et al., Chem. Abstracts, vol. 70, 1969; 66242g.
Krieg, M. et al. "Self-Sensitized Photooxidation..." J. Am. Chem. Soc., American Chemical Society 1984, 106, pp. 2477–2479.
Richard L. Lipton, et al, The Use of a Derivative of Hematoporphyrin in Tumor Detection, vol. 26, No. 1, Jan. 1961, Journal of the National Cancer Institute.

*Primary Examiner*—Mukund J. Shah
*Assistant Examiner*—P. K. Sripada
*Attorney, Agent, or Firm*—Ladas & Parry

[57] ABSTRACT

New complex salts of hematoporphyrin and of its derivatives have the general Formula 1 (FIG. 1). The method of preparation of new complex salts of Formula 1 consists of reacting, with a basic amino acid, hematoporphyrin derivatives of general Formula 4 (FIG. 4). The new complex salts are used as a therapeutic agent for detection and treatment of neoplasms.

13 Claims, 6 Drawing Sheets

COMPLEX SALTS OF HEMATOPORPHYRIN AND OF ITS DERIVATIVES, THEIR SYNTHESIS, AND THERAPEUTIC AGENT

FIELD OF INVENTION

The present invention relates to complex salts of hematoporphyrin and of its derivatives, their synthesis, and therapeutic agent.

The new salts of hematoporphyrin and of its derivatives are intended to be used for detection and treatment of neoplasms.

BACKGROUND OF INVENTION

Since more than a decade hematoporphyrin and its derivatives /HpD/ serve as photosensitizers applied for detection and destruction of neoplasms in humans and animals. These compounds are injected intravenously and are translocated via active transport to various body organs. In healthy tissues they remain for a relatively short time, as they are metabolized and excreted, whereas in neoplastic tissues they are retained and remain there for several days on an unchanged level. This feature was utilized in the photodynamic method for the diagnosis and selective destruction of neoplastic tissues. Since all hematoporphyrin derivatives are sparingly soluble in water, preparation of their aqueous solutions was so far very troublesome.

In "Cancer Research", v.44, p. 1924,1984 /see also ibid, v. 45, p.635,1985/ a method for obtainment of hematoporphyrin preparations to be used for injections was reported. According to this method, hematoporphyrin derivatives are disolved in a NaOH solution, stirred for 1 h and adjusted to pH ca. 7.1 with 0.1N HCl. This is very inconvenient, since even slight exceeding of pH below 7.0 causes precipitation of the compound. The final solution is prepared by adding an appropriate amount of saline. The solution is sterilized and stored in sealed ampoules. These agueous solutions are unstable on account of the strong tendency of all hematoporphyrin derivatives for aggregation. According to the quoted paper, the solutions remain stable for ca. 3 months provided they are refrigerated /at <20° C./ in the dark.

SUMMARY OF THE INVENTION

The present invention provides new water-soluble complex salts of hematoporphyrin and of its derivatives, whose solutions have pH between 7.2-7.8/in dependence on concentration/ this enabling rapid preparation of a solution well soluble in water or saline, as well allowing for better bioavailability of the therapeutic agent.

Unexpectedly, it was found that the therapeutic activity of the new complex salts exceeds that of, e.g., the known sodium salts of hematoporphyrin and of its derivatives /HpD $Na_2$/. Moreover, the new salts inhibit—without irradiation—the development of neoplastic cells, as confirmed by studies of cell lines.

DETAILED DESCRIPTION

Figure 1:
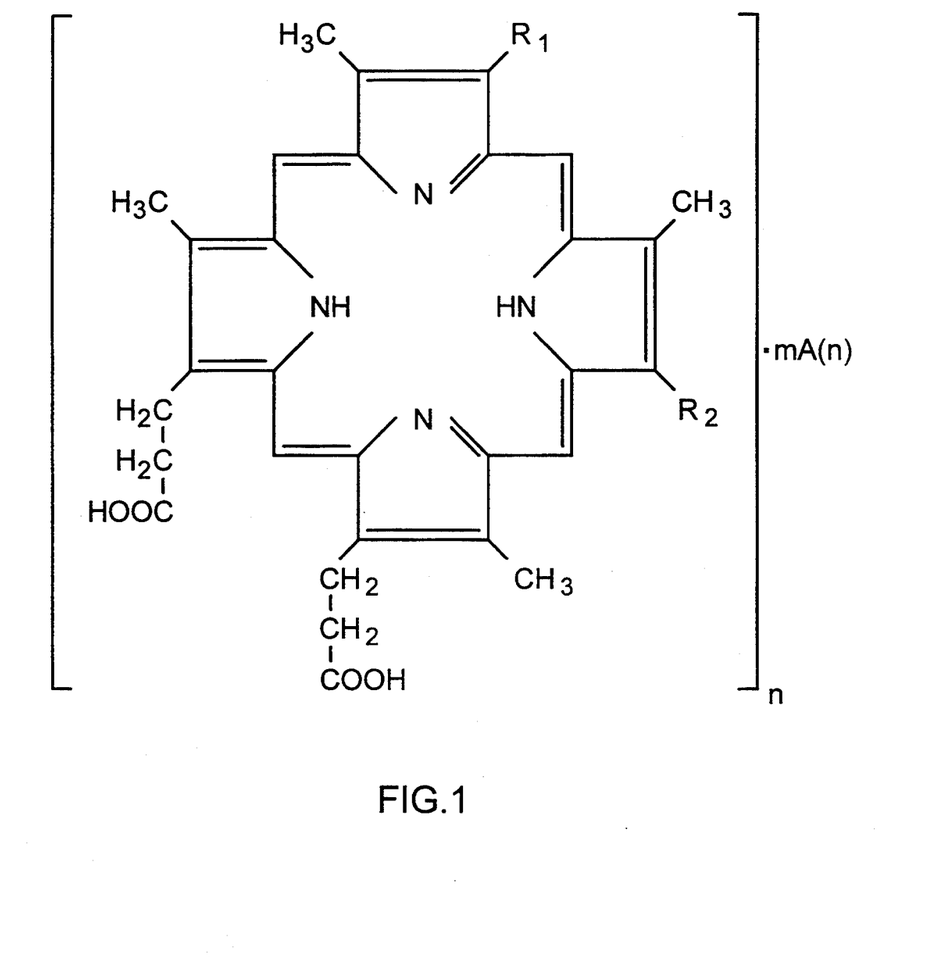
FIG. 1 is a formula (Formula 1) showing salts of hematoporphyrin and its derivatives according to the invention.
Figure 2:
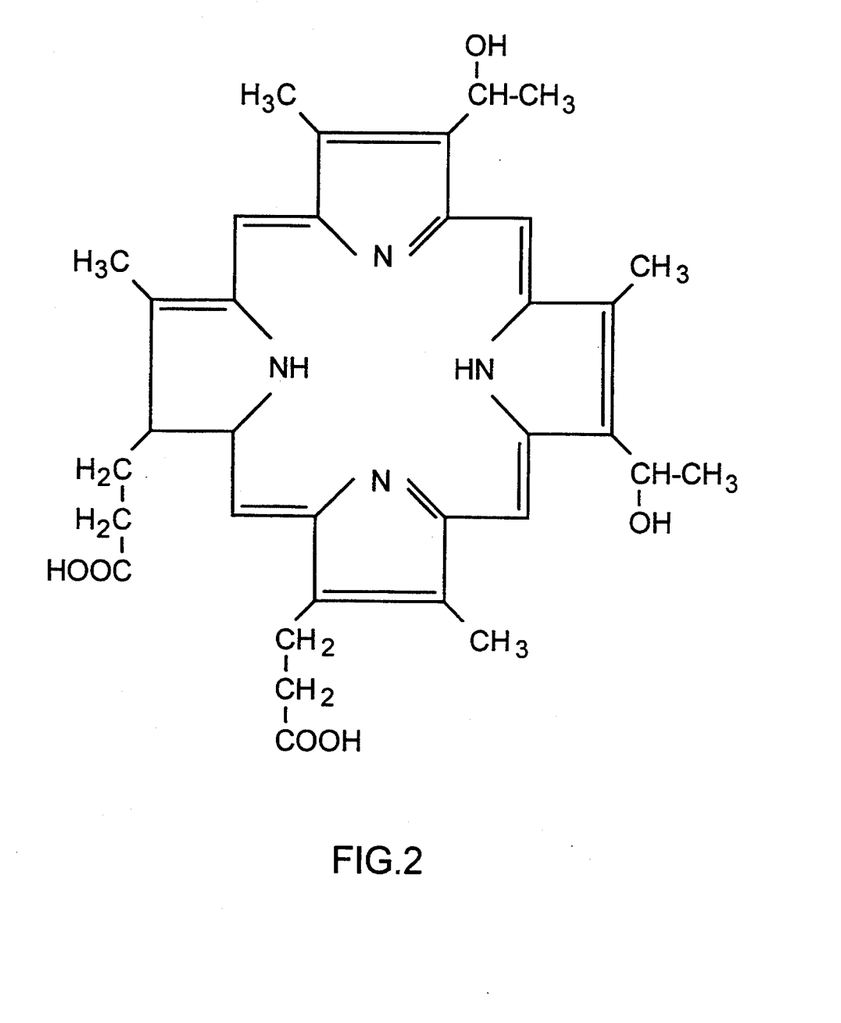
FIG. 2 is a formula (Formula 2) showing a monomer from which the salts of the invention may be derived.

According to the invention, salts of hematoporphyrin and of its derivatives have the general formula 1, in which $R^1$ and $R^2$ are identical or different, and denote the groups: $-CH=CH_2$, $-CH/OH/-CH_3$, $-CH/OR^3/-CH_3$, where $R^3$ represents the group forming the oligomer containing ethereal and/or ester bindings, which comprises from 1 to 5 identical or different units derived from the monomer of formula 2 or $R^1$ and $R^2$ are identical and denote the group $-CH/R^4/-CH_3$, where $R^4$ represents the following groups: carboxymethylamino, 1-carboxyethylamino, 1-carboxy-2-methyl-propyl-amino, 1-carboxy-3-methyl-butylamino, 1-carboxy-2-methyl-butylamino, 1-carboxy-butylamino, 1-carboxy-pentylamino, 1-carboxy-2-hydroxy-ethylamino, 1-carboxy-2-hydroxy-propylamino, 1-carboxy-2-mercapto-ethylamino, 1-carboxy-3-methylthio-propylamino, 1,2-dicarboxyethyl-amino 1-carboxy-2-carbamoyl-ethylamino, 1,3-dicarboxy-propylamino, 1-carboxy-3-carbamoyl-propylamino, 1-carboxy-2-phenyl-ethylamino, 1-carboxy-2-/4-hydroxyphenyl/-ethylamino, 1-carboxy-2-indolyl-ethylamino, 2-carboxy-pyrrolidinyl, 2-carboxy-4-hydroxy-pyrrolidinyl, 1-carboxy-5-amino-pentylamino, 1-carboxy-4-guanidyl-butyl-amino, 1-carboxy-4-hydroxy-5-amino-pentylamino or 1-carboxy-2-/1H-imidazole/-ethylamino group; A denotes a basic amino acid; m amounts to 2-6; n is 1-5.

Figure 3:
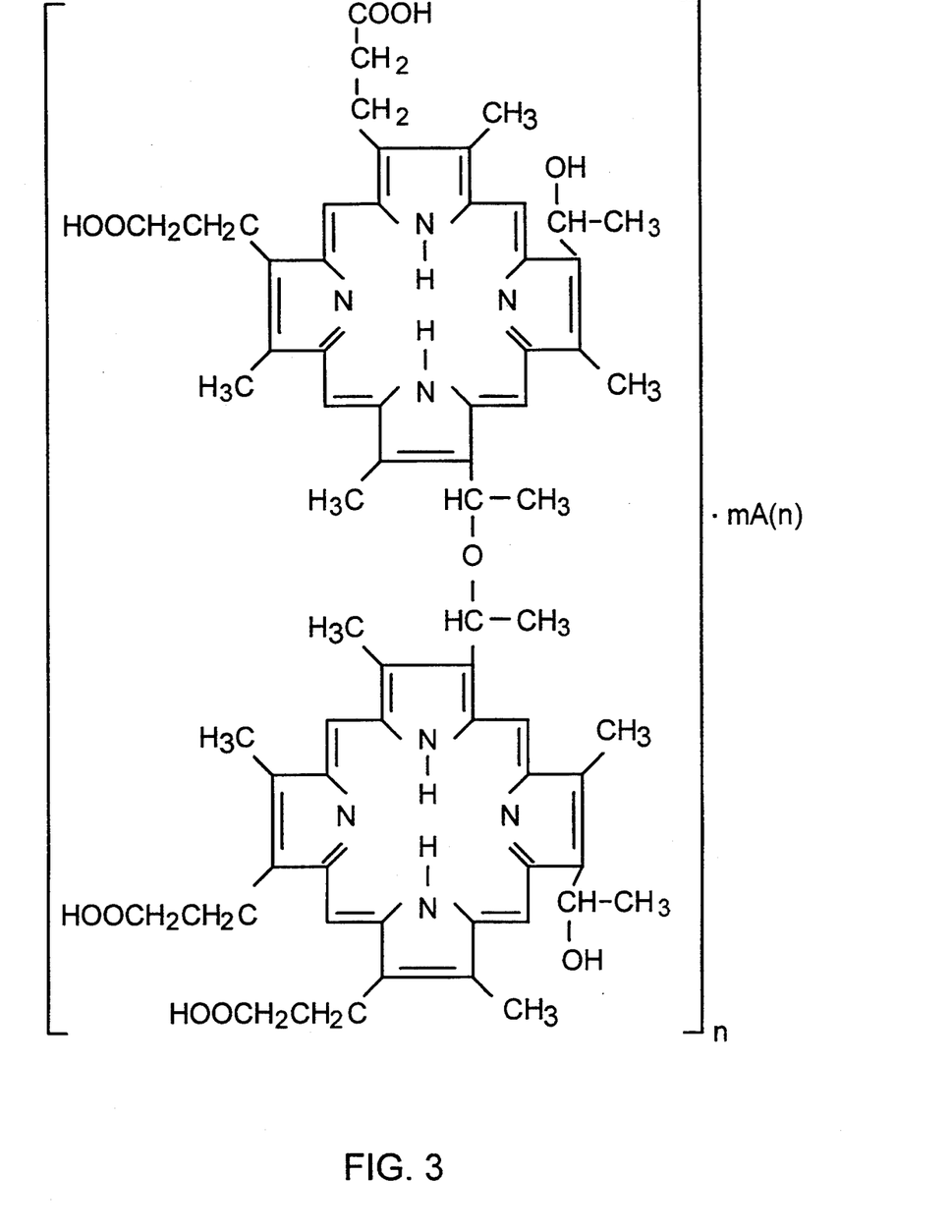
FIG. 3 is a formula (Formula 3) showing preferred salts of hematoporphyrin according to the invention.
Figure 5:
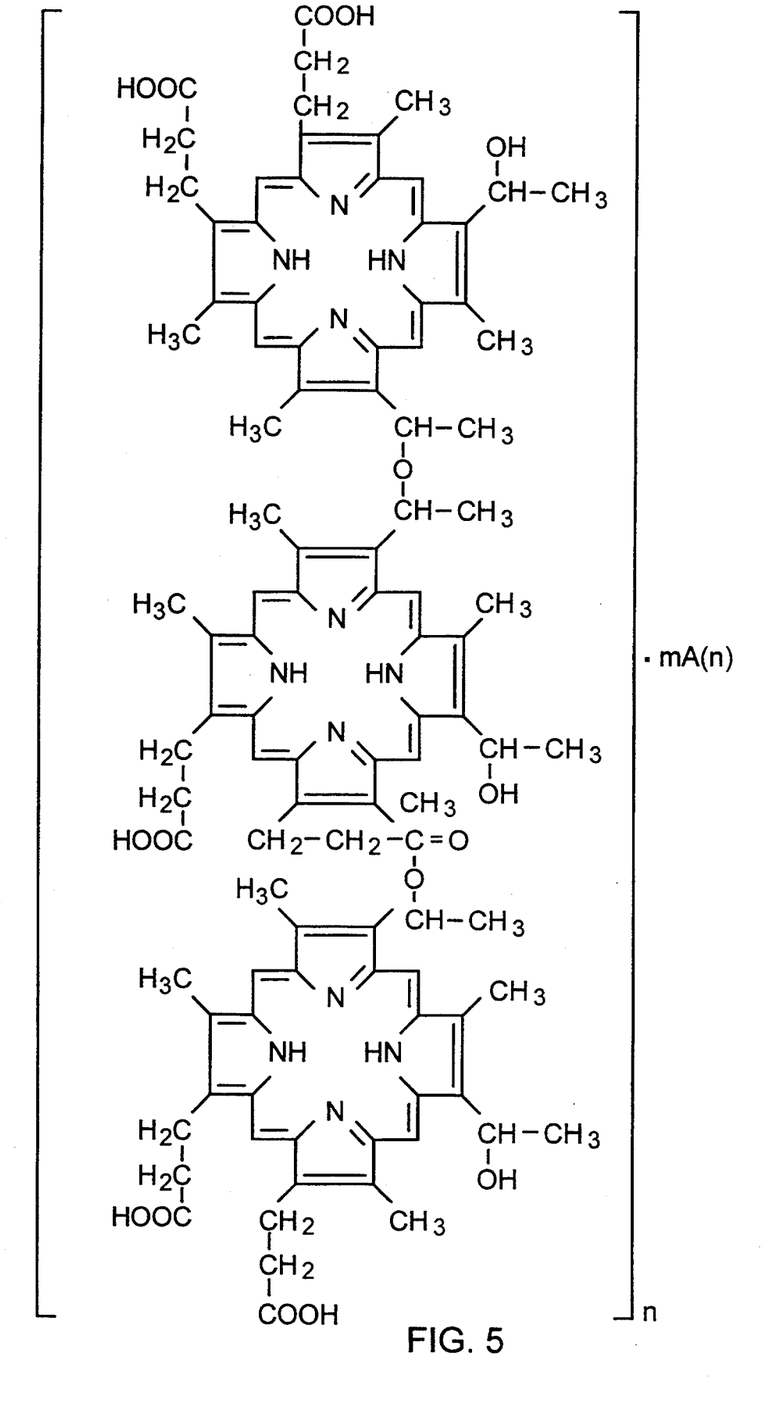
FIG. 5 is a formula (Formula 5) showing preferred salts of hematoporphyrin according to the invention.

The present invention also provides mixtures of salts of formula 1 and aggregations of these salts. Preferred amino acids of symbol A comprise these with isoelectric point exceeding 7/particularly l-arginine, lysine, histidine or hydroxylysine/. Advantageous salts include those of formula 1, in which $R^1$ and $R^2$ are identical and denote the $-CH/R^4/-CH_3$ group and salts of ether of formula 3 and salts of formula 5. Preferred mixtures comprise those containing amino acid salts of hematoporphyrin, protoporphyrin, vinyldeuteroporphyrin and dihematoporphyrin ether, or possibly their aggregations.

Figure 4:
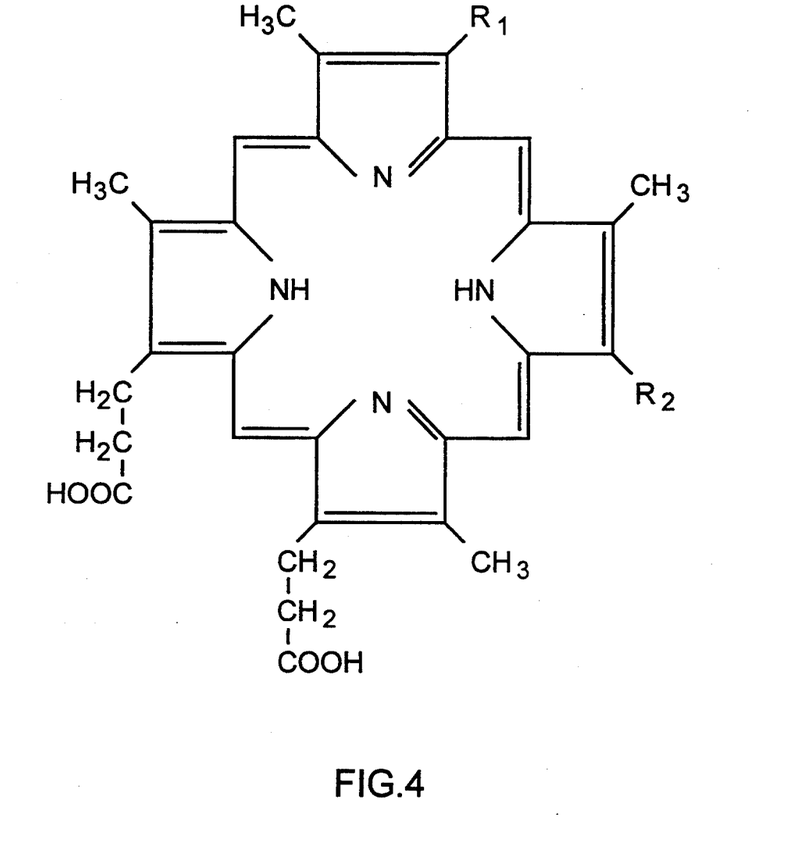
FIG. 4 is a (Formula 4) showing a preferred starting compound for preparing the salts of the invention.

According to the invention, in the method for synthesizing complex salts of hematoporphyrin and of its derivatives of general formula 1, or mixtures of salts of general formula 1, in which the meaning of the symbols is as above-mentioned, a hematoporphyrin derivative of general formula 4 or a mixture of at least two derivatives of general formula 4, in which the meaning of $R^1$ and $R^2$ is as above-mentioned, provided that if $R^1$ and $R^2$ denote the $-CH/R^4/-CH_3$ group, then the carboxy groups of the $R^4$ substituent may be free or protected, is reacted with a basic amino acid with free or protected carboxy groups or with its monohydrochloride, preferably in organic solvent, in a mixture of organic solvents or in a medium containing organic solvent and water or a mixture of organic solvents and water, possibly the groups protecting the carboxy functions are removed, and the product being a salt of formula 1 or a mixture of salts of formula 1, possibly containing aggregations of salts of formula 1, is isolated.

In the process according to the invention the reactions of the amino groups of amino acids with the carboxy groups of the hematoporphyrin derivatives form ionic systems according to the equation:

$$-COOH + H_2N-R \rightarrow -COO^- + {}^+H_3N-R$$

Amino acids with isoelectric point >7, particularly arginine, lysine, histidine or hydroxylysine, are applied as the basic amino acid.

For protection of the carboxy groups in the starting compounds, use can be made of various known blocking groups, e.g., those described in "Protective Groups in Organic Synthesis", T. W. Green, John Wiley and Sons, 1981. These groups are exemplified by those forming alkyl, benzyl or silyl esters, as well as by other groups applied for protection of the carboxy functions.

The reaction may proceed within a wide temperature range, preferably from room temperature to 100° C., particularly between 50°-70° C. Reaction time is usually from several min to more than 10 hs.

Advantageous organic solvents comprise amides e.g. formamide, dimethylformamide, diethylformamide, nitriles e.g. acetonitrile, propionitrile, isobutyronitrile, esters e.g. ethyl acetetate, ketones e.g. acetone, sulphoxides e.g. dimethylsulphoxide, alcohols and ethyl carbonate, or their mixtures. The reaction is usually carried out in aqueous-organic medium.

Blocking groups, if present, are removed by known procedures, e.g. by hydrolysis or hydrogenolysis.

The salt or a corresponding mixture of salts of formula 1 can be isolated from the reaction mixture by different methods, e.g. by precipitation, crystallization and other known procedures. A particularly advantageous method consists of addition, to the reaction mixture, of a solvent or of a mixture of low-polarity solvents which, however, form with the solvent used in the reaction a homogeneous solution at a ratio from 1:1 to 1:5. Appropriate solvents include e.g. ethyl, ether or acetone. The resulting mixture is left to stand from several to more than 10 hs for slow precipitation of the product. The precipitate is separated by filtration, washed and dried under vacuum over drying agent, preferably $P_2O_5$. The products are stable and do not deliquesce. They have to be protected from light. The isolation stage possibly comprises separation of the product mixture.

Starting compounds of formula 4 are known. They may be prepared from hemin.

The invention also provides a therapeutic agent for detection and/or treatment of neoplasms, containing a salt of general formula 1, in which the meaning of the symbols is as above-mentioned, or a mixture of at least two salts of formula 1 and possibly their aggregations.

The mixture can be exemplified by one containing amino acid salts of hematoporphyrin, protoporphyrin, vinyldeuteroporphyrin and dihematoporphyrin ether, and possibly their aggregations.

According to the invention, the therapeutic agent may consist of a salt of formula 1 or of a mixture of salts of formula 1 in solid state, preferably stored in a sterile tight container.

The sterile tight container usually contains the salt or salt mixture in a therapeutically effective dose. In general, the therapeutically effective dose amounts to 1.5–10 mg/kg body weight. From the salt stered in the container, sterile aqueous solutions for direct parenteral administration can be prepared very rapidly.

According to the invention, the therapeutic agent may also be produced in the form of ready-for-use preparations. In this case the active substance, i.e. a salt or a mixture of salts of formula 1, is mixed with a pharmacologically admissible diluent and/or carrier. The therapeutic agent is usually administered by injection, particularly intravenously, but it may also be applied intraperitoneally or rectally. The preparation can be exemplified by a sterile aqueous solution. The aqueous solution may, apart from the salt of formula 1, possibly contain saline and—if necessary—propylene glycol. As above-mentioned, these solutions may be applied immediately after preparation or can be stored in sterile containers.

According to the invention, the therapeutic agent may be applied without irradiation; it is more effective, however, as a photosensitizer in the photodynamic method for the diagnosis and therapy of neoplasms.

New compounds of formula 1 were tested on cell lines. Use was made of 9 different neoplastic cell lines which were incubated for 48 hs with various new salts of protoporphyrin and with a new salt of the conventionally applied HpD preparation/hematoporphyrin derivatives/obtained according to Lipson et al. All compounds were used in the form of aqueous solutions, at a concentration of 50 mcg/ml. Determination was made of:

1/ Cell fluorescence /F/: after 48 hs incubation, the cells were washed away, the intensity of fluorescence was measured in a fluorescence microscope and was expressed on an arbitrary scale of 0–4 scores;
2/ Percentage of living cells /P %/ after 48 hs incubation;
3/ Cell multiplication coefficient /M/ in the presence of different preparations, expressed as:

$$M = \frac{\text{Multiplied cell count in culture with the tested preparation at a concentration of 50 mcg/ml after 48 hs}}{\text{Multiplied cell count in control culture after 48 hs}}$$

The results are presented in Tables 1,2,3. They indicate that compounds of formula 1 differ in affinity to the various cell lines tested, and exert dissimilar effects on their survival. When different derivatives are available, it is possible to select the one most active against the given type of neoplasm, this extending the range of effective therapy.

Symbols used in Tables 1–3 represent the following compounds:

PP/Asp/$_2$/Arg/$_2$-l-arginine di/N-aspartyl/-protoporphyrinate
PP/Glu/$_2$/Arg/$_2$-l-arginine di/N-glutamyl/-protoporphyrinate
PP/Cys/$_2$/Arg/$_2$-l-arginine di/N-cysteyl/-protoporphyrinate
PP/Ala/$_2$/Arg/$_2$-l-arginine di/N-alanyl/-protoporphyrinate
PP/Ser/$_2$/Arg/$_2$-l-arginine di/N-seryl/-protoporphyrinate
PP/Lys/$_2$/Arg/$_2$-l-arginine di/N-lysyl/-protoporphyrinate
PP/Arg/$_2$/Arg/$_2$-l-arginine di/N-arginyl/-protoporphyrinate
PP/Trp/$_2$/Arg/$_2$-l-arginine di/N-tryptophanyl/-protoporphyrinate PP/Met/2/Arg/2-l-arginine di/N-methionyl-protoporphyrinate Tables 1–3 contain the following symbols of cell lines used in studies of the antineoplastic agents: derivatives of protoporphyrin and of the HpD preparation:

| | Human neoplasm lines: |
|---|---|
| Hep-2 | larynx cancer cells |
| Hela | cervix uteri cancer cells |
| KB | oral cavity cancer cells |
| HBT-39/w | breast cancer cells |
| T-47D | breast cancer cells |
| P3HR1 | Burkitt lymphadenoma cells |
| | Murine neoplasm lines: |
| GRMT/F6 | mammary gland cancer cells of GR-strain mice |
| $M_m$5MT/C1 | mammary gland cancer cells of C3H-strain mice |
| MA-104 | Rhesus monkey embryo kidney cancer cells. |

As compared with the known HpD preparation, the new salts display a wider range of the ability to penetrate into various types of neoplastic cells and exhibit higher effectiveness of their destruction. For example, upon use of the new l-arginine salt of HpD [HpD/Art/2], the percentage of living cells after 48 hs incubation /P %/ amounts for the Hela line, MA-104 line and HBT-39/w line to 13,6 and 0% respectively, whereas upon application of the known preparation, i.e. of the sodium salt of HpD /HpD Na2/ the respective values are much higher, amounting to 28, 17 and 10%.

The new compounds were also studied in animals. We selected the compound PP/Lys/2/Arg/2/compound used in the example XVII being one of the most active ones in studies of the Mm5MT/C1 cell line /mammary gland cancer of C3H mice/, as well as PP/Glu/2/Arg/2 used in the example XV/ being least effective against this type of neoplasm.

Figure 6:
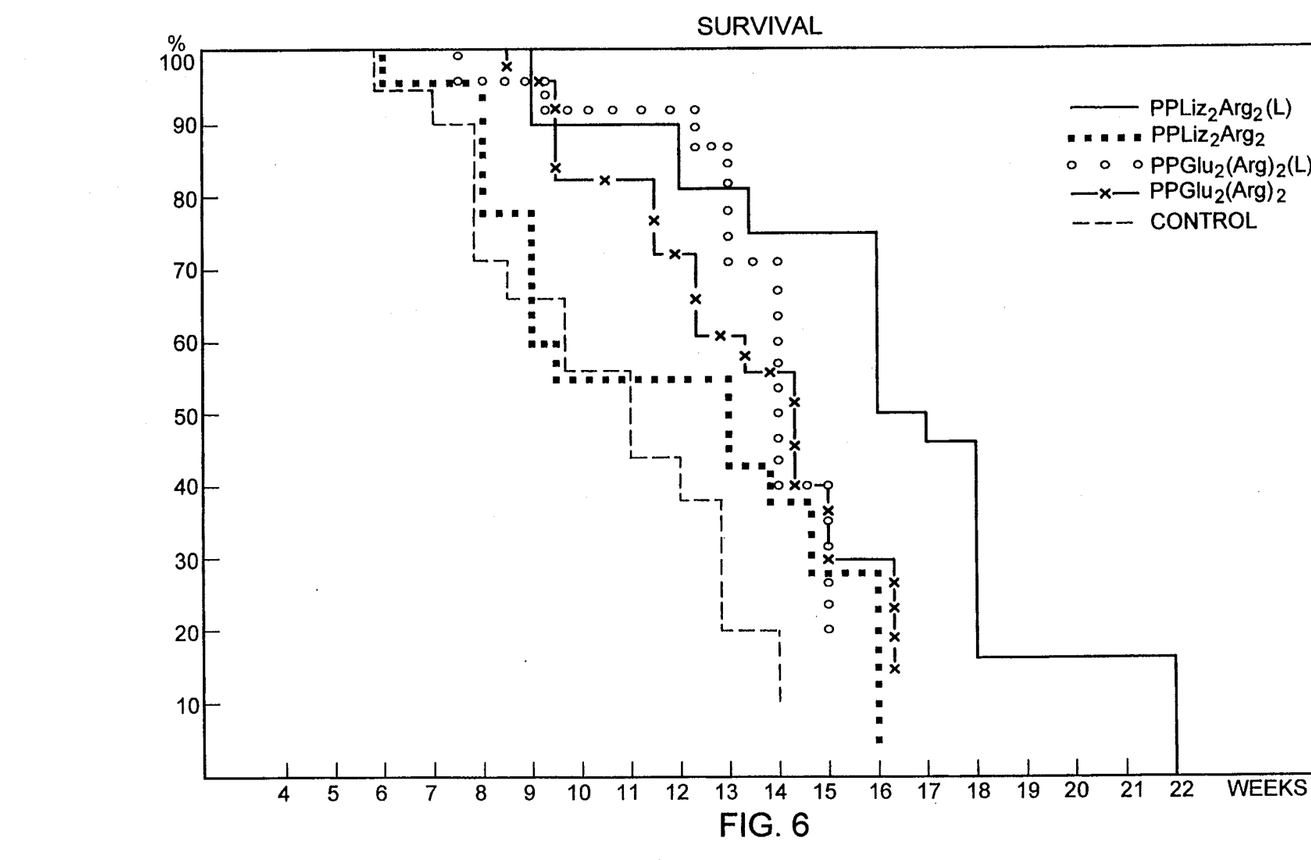
FIG. 6 is a graph showing the survival rate of C3H mice with transplanted mammary gland cancer after administration of compounds of the invention (with and without irradiation) and a control.

In animal studies, C3H mice with transplanted mammary gland cancer were administered both above-mentioned compounds in a dose of 10 mg/kg body weight, in two variants: mice irradiated with He-Ne laser in a dose of 150 J/cm$^2$/in FIG. 6, marked by the letter L next to the symbol of the compound/and not irradiated ones. The results are recorded in the Figure. They indicate that:

1/ animal studies confirmed the results obtained in cell line experiments;
2/ the PP/Lys/2/Arg/2 preparation proved to be most active, greatly prolonging mice survival;
3/ the amino acid derivatives of protoporphyrin exert a cytotoxic effect on neoplastic cells; this effect is stronger in the case of laser-irradiated cells, as compared with the not irradiated ones.

EXAMPLES OF PREPARATION OF COMPLEX SALTS OF HEMATOPORPHYRIN AND OF ITS DERIVATIVES

Example I

HpD is a mixture of hematoporphyrin derivatives, such as hematoporphyrin, protoporphyrin, vinyl-deuteroporphyrin, dihematoporphyrin ether or their aggregations. To 1 g HpD of mean molecular weight of 600/1.67 mmol/, dissolved in 30 ml dimethylformamide/DMF/, 581.8 mg l-arginine/3.34 mmol/dissolved in 2 ml of water were added. The mixture was heated for 15–20 min at 60° C. on a water bath with intensive stirring. Subsequently 100 ml of acetone were added, and stirring was continued for 3–5 min. The solution was left to stand for 5–15 hs. During this period the salt mixture denoted HpD/Arg/2 precipitated. The precipitate was filtered off, washed with ether and dried under vacuum. After drying under vacuum the precipitate is stable on air; it has to be protected from light, because of its content of porphyrin derivatives. The yield of the reaction is ca.75%.

Example II

To 1 g HpD dissolved in 20 ml of formamide, 581.8 mg l-arginine dissolved in 2 ml of water were added. The solution was heated and stirred as in example I. Subsequently, after cooling, 100 ml of ethyl ether were added. The solution was stirred and left to stand for several hours. The precipitate formed was filtered off, washed with ether and dried under vacuum. The mixture of salts HpD/Arg/2 was obtained in an amount of 1264.8 g, this corresponding to an 86% yield.

Example III

To 1230 mg dilysylprotoporphyrin PP/Lys/2/1.4 mmol/dissolved in 40 ml of formamide, 490 mg l-arginine/2.8 mmol/dissolved in 1.5 ml of water were added. The mixture was heated in a water bath at 60° C. for ca.20 min. After cooling, 100 ml of ethyl ether were added, the solution was stirred and left to stand for several hs. The precipitate formed was washed with ether and dried under vacuum. The product was obtained in an amount of 1630 mg, this representing a 90% yield. The analytical data of the product are given for the number XXI in Table 4.

Example IV

To 1199.6 mg/1.4 mmol/of diglutamylprotoporphyrin dissolved in 60 ml of formamide, 409.3 mg l-lysine dissolved in 1.5 ml of water were added. The solution was heated at 60° C. for 30 min, whereupon 120 ml of an acetone-ether/1:3/mixture were added; then the mixture was stirred for 10 min and was left to stand for several hours. The precipitate formed was filtered off under vacuum, washed with ethyl ether and dried under vacuum over P$_2$O$_5$. The amount of the product was 1575 mg, this corresponding to a 97.8% yield.

Example V

To 1081.8 mg/1.4 mmol/diserylprotoporphyrin dissolved in 50 ml of formamide, 490 mg l-arginine/2.8 mmol/dissolved in 1.5 ml of water were added. The solution was heated at 60° C. for 30 min, whereupon 120 ml of an acetone-ether/1:3/mixture were added; then the mixture was stirred for 50 min and subsequently was left to stand for several hours for crystallization. The precipitate formed was filtered off under vacuum and dried under vacuum over P$_2$O$_5$. The amount of the product was 1500 mg, this representing a 95.5% yield.

All salts recorded in Table 4 were prepared by the procedure described in Example V. They include:

PP/Ser/2/Arg/2-l-arginine di/N-seryl/protoporphyrinate
PP/Gly/2/Arg/2-l-arginine di/N-glycyl/protoporphyrinate
PP/Ala/2/Arg/2-l-arginine di/N-alanyl/protoporphyrinate
PP/Val/2/Arg/2-l-arginine di/N-valyl/protoporphyrinate
PP/Leu/2/Arg/2-l-arginine di/N-leucyl/protoporhyrinate
PP/ILeu/2/Arg/2-l-arginine di/N-isoleucyl/protoporphyrinate PP/Phen/2/Arg/2-l-arginine di/N-phenylalanyl/protoporphyrinate PP/Tyr/2/Arg/2-l-arginine di/N-tyrosyl/protoporphyrinate PP/Pro/2/Arg/2-l-arginine di/N-prolyl/protoporphyrinate PP/ProOH/2/Arg/2-l-arginine di/N-dihydroxyprolyl/protoporphyrinate PP/Trp/2/Arg/2-l-arginine di/N-tryptophanyl/protoporphyrinate PP/Cys/2/Arg/2-l-arginine di/N-cysteyl/protoporphyrinate PP/Met/2/Arg/2-l-arginine di/N-methionyl/protoporphyrinate PP/Asp/2/Arg/2-l-arginine di/N-aspartyl/protoporphyrinate PP/Glu/2/Arg/2-l-arginine di/N-glutamyl/protoporphyrinate PP/Arg/2/Arg/2-l-arginine di/N-arginyl/protoporphyrinate PP/Lys/2/Arg/2-l-arginine di/N-lysyl/protoporphyrinate PP/LysOH/2/Arg/2-l-arginine di/N-hydroxylysyl/protoporphyrinate PP/His/2/Arg/2-l-arginine di/N-histidyl/protoporphyrinate PP/Asn/2/Arg/2-l-arginine di/N-asparginyl/protoporphyrinate PP/Gln/2/Arg/2-l-arginine di/N-glutaminyl/protoporphyrinate

TABLE 1

| | | Cell line | | | | | | | | | | |
|---|---|---|---|---|---|---|---|---|---|---|---|---|
| | Symbol of the | Hela | | | MA - 104 | | | CL | | | PZ | | |
| No | compound | F | P % | M | F | P % | M | F | P % | M | F | P % | M |
| 1 | HpD/Arg/2 | + | 13 | 0,14 | slad | 6 | 0,05 | − | 30 | 0,30 | − | 30 | 0,30 |
| 2 | PP/Asp/2/Arg/2 | +++ | 38 | 0,50 | +++ | 17 | 0,52 | + | 55 | 0,55 | + | 14 | 0,15 |
| 3 | PP/Glu/2/Arg/2 | ++ | 33 | 0,16 | − | 15 | 0,16 | − | 45 | 0,45 | + | 15 | 0,15 |
| 4 | PP/Cys/2/Arg/2 | ++ | 55 | 0,43 | ++ | 11 | 0,16 | − | 30 | 0,30 | + | 40 | 0,40 |
| 5 | PP/Ala/2/Arg/2 | + | 11 | 0,11 | ++ | 50 | 0,50 | − | 30 | 0,30 | ++ | 15 | 0,15 |
| 6 | PP/Ser/2/Arg/2 | ++ | 55 | 0,50 | − | 0 | 0,16 | + | 0 | 0 | ++ | 2,5 | 0,02 |
| 7 | PP/Liz/2/Arg/2 | +++ | 16 | 0,16 | − | 0 | 0,10 | + | 30 | 0,30 | + | 50 | 0,50 |
| 8 | PP/Fen/2/Arg/2 | +++ | 5 | 0,14 | ++ | 35 | 0,35 | ++ | 0 | 0 | + | 8 | 0,08 |
| 9 | PP/Arg/2/Arg/2 | ++++ | 11 | 0,28 | ++ | 31 | 0,42 | ++ | 4 | 0,03 | + | 10 | 0,10 |
| 10 | PP/Trp/2/Arg/2 | +++ | 62 | 0,62 | + | 25 | 0,25 | − | 50 | 0,50 | + | 50 | 0,50 |
| 11 | PP/Met/2/Arg/2 | ++++ | 5 | 0,05 | ++ | 22 | 0,33 | + | 0 | 0 | + | 8 | 0,08 |

TABLE 2

| | | Cell line | | | | | | | | |
|---|---|---|---|---|---|---|---|---|---|---|
| | Symbol of the | KB | | | HBT - 39/w | | | GR | | |
| No | compound | F | P % | M | F | P % | M | F | P % | M |
| 1 | HpD/Arg/2 | ++++ | 9 | 0,08 | +++ | 0 | 0 | ++ | 20 | 0,40 |
| 2 | PP/Asp/2/Arg/2 | ++ | 16 | 0,12 | +++ | 48 | 0,81 | ++ | 25 | 0,73 |
| 3 | PP/Glu/2/Arg/2 | ++++ | 8 | 0,08 | + | 66 | 0,73 | + | 75 | 0,75 |
| 4 | PP/Cys/2/Arg/2 | + | 12 | 0,12 | + | 42 | 0,53 | +++ | 50 | 0,75 |
| 5 | PP/Ala/2/Arg/2 | +++ | 0 | 0 | ++ | 17 | 0,33 | + | 50 | 0,50 |
| 6 | PP/Ser/2/Arg/2 | ++ | 0 | 0 | ++ | 33 | 0,50 | + | 12 | 0,12 |
| 7 | PP/Liz/2/Arg/2 | − | 12 | 0,12 | ++++ | 47 | 0,44 | +++ | 25 | 0,75 |
| 8 | PP/Fen/2/Arg/2 | ++ | 12 | 0,12 | ++++ | 11 | 0,11 | +++ | 0 | 0 |
| 9 | PP/Arg/2/Arg/2 | + | 16 | 0,16 | ++++ | 28 | 0,28 | +++ | 12 | 0,12 |
| 10 | PP/Trp/2/Arg/2 | nb | 21 | 0,21 | ++++ | 18 | 0,11 | +++ | 62 | 0,62 |
| 11 | PP/Met/2/Arg/2 | ++ | 5 | 0,12 | ++++ | 8 | 0,08 | ++++ | 25 | 0,22 |

TABLE 3

| | | Cell line | | | | | | | | |
|---|---|---|---|---|---|---|---|---|---|---|
| | Symbol of the | HEp - 2 | | | Mm | | | T- 47D | | |
| No | compound | F | P % | M | F | P % | M | F | P % | M |
| 1 | HpD/Arg/2 | + | 31 | 0,31 | ++ | 33 | 0,75 | + | 30 | 0,66 |
| 2 | PP/Asp/2/Arg/2 | +++ | 47 | 0,40 | +++ | 70 | 0,92 | ++++ | 65 | 0,92 |
| 3 | PP/Glu/2/Arg/2 | ++++ | 15 | 0,08 | +++ | 76 | 0,70 | +++ | 49 | 0,80 |
| 4 | PP/Cys/2/Arg/2 | ++++ | 60 | 0,32 | +++ | 40 | 0,73 | + | 26 | 0,84 |
| 5 | PP/Ala/2/Arg/2 | ++ | 21 | 0,21 | +++ | 86 | 0,84 | +++ | 85 | 0,82 |
| 6 | PP/Ser/2/Arg/2 | + | 25 | 0,50 | + | 37 | 0,37 | +++ | 40 | 0,60 |
| 7 | PP/Liz/2/Arg/2 | ++ | 10 | 0,42 | ++ | 33 | 0,80 | ++ | 57 | 0,92 |
| 8 | PP/Fen/2/Arg/2 | ++ | 3 | 0,08 | ++++ | 12 | 0,37 | + | 60 | 0,60 |
| 9 | PP/Arg/2/Arg/2 | + | 5 | 0,14 | +++ | 12 | 0,38 | +++ | 40 | 0,40 |
| 10 | PP/Trp/2/Arg/2 | +++ | 15 | 0,15 | +++ | 11 | 0,33 | + | 13 | 0,13 |
| 11 | PP/Met/2/Arg/2 | +++ | 0 | 0 | ++++ | 8 | 0,08 | +++ | 10 | 0,10 |

TABLE 4

| Example | Symbol of the compound | Molecular formula | Gram-molecular weight | C calc. % | C found % | H calc. % | H found % | N calc. % | N found % |
|---|---|---|---|---|---|---|---|---|---|
| 1 | 2 | 3 | 4 | 5 | 6 | 7 | 8 | 9 | 10 |
| V | PP/Ser/2Arg/2 | $C_{52}H_{76}N_{14}O_{12}$ | 1121,2 | 55,65 | 55,69 | 6,78 | 6,81 | 17,48 | 17,52 |
| VI | PP/Gli/2/Arg/2 | $C_{50}H_{72}N_{14}O_{12}$ | 1061,2 | 56,53 | 56,42 | 6,78 | 6,71 | 18,45 | 18,22 |

TABLE 4-continued

| Example 1 | Symbol of the compound 2 | Molecular formula 3 | Gram-molecular weight 4 | C calc. % 5 | C found % 6 | H calc. % 7 | H found % 8 | N calc. % 9 | N found % 10 |
|---|---|---|---|---|---|---|---|---|---|
| XII | PP/Ala/$_2$/Arg/$_2$ | C$_{52}$H$_{76}$N$_{14}$O$_{12}$ | 1089,2 | 55,09 | 55,14 | 6,97 | 7,02 | 17,99 | 18,03 |
| VIII | PP/Wal/$_2$/Arg/$_2$ | C$_{56}$H$_{84}$N$_{14}$O$_{12}$ | 1145,3 | 58,67 | 58,58 | 7,33 | 7,24 | 17,11 | 17,00 |
| IX | PP/Leu/$_2$/Arg/$_2$ | C$_{58}$H$_{75}$N$_{14}$O$_{12}$ | 1173,3 | 59,32 | 59,24 | 6,39 | 6,27 | 16,71 | 16,64 |
| X | PP/Leu/$_2$/Arg/$_2$ | C$_{58}$H$_{75}$N$_{14}$O$_{12}$ | 1173,3 | 59,32 | 59,34 | 6,39 | 6,41 | 16,71 | 16,68 |
| XII | PP/Fen/$_2$/Arg/$_2$ | C$_{64}$H$_{84}$N$_{14}$O$_{12}$ | 1241,4 | 61,86 | 61,91 | 6,78 | 6,72 | 15,78 | 15,74 |
| XII | PP/Tyr/$_2$/Arg/$_2$ | C$_{64}$H$_{84}$N$_{14}$O$_{14}$ | 1273,4 | 60,31 | 60,39 | 6,44 | 6,46 | 15,39 | 15,45 |
| XIII | PP/Pre/$_2$/Arg/$_2$ | C$_{56}$H$_{80}$N$_{14}$O$_{12}$ | 1141,3 | 58,88 | 58,93 | 7,01 | 7,07 | 17,17 | 17,21 |
| XIV | PP/PreOH/$_2$/Arg/$_2$ | C$_{56}$H$_{80}$N$_{14}$O$_{14}$ | 1175,3 | 57,18 | 57,09 | 6,80 | 6,72 | 16,67 | 16,59 |
| XV | PP/Trp/$_2$/Arg/$_2$ | C$_{68}$H$_{86}$N$_{14}$O$_{12}$ | 1319,4 | 61,84 | 61,72 | 6,52 | 6,46 | 16,98 | 16,79 |
| XVI | PP/Cys/$_2$/Arg/$_2$ | C$_{52}$H$_{76}$N$_{14}$O$_{12}$S | 1153,3 | 54,01 | 54,11 | 6,59 | 6,64 | 16,99 | 17,04 |
| XVII | PP/Met/$_2$/Arg/$_2$ | C$_{56}$H$_{84}$N$_{14}$O$_{12}$S$_2$ | 1209,4 | 55,56 | 55,61 | 6,94 | 7,01 | 16,20 | 16,27 |
| XVIII | PP/Asp/$_2$/Arg/$_2$ | C$_{54}$H$_{76}$N$_{14}$O$_{16}$ | 1177,2 | 55,05 | 55,11 | 6,46 | 6,52 | 16,65 | 16,74 |
| XIX | PP/Glu/$_2$/Arg/$_2$ | C$_{56}$H$_{80}$N$_{14}$O$_{16}$ | 1205,3 | 55,75 | 55,64 | 6,64 | 6,53 | 16,26 | 16,18 |
| XX | PP/Arg/$_2$/Arg/$_2$ | C$_{58}$H$_{90}$N$_{20}$O$_{12}$ | 1339,4 | 51,96 | 51,82 | 6,72 | 6,64 | 20,90 | 20,97 |
| XXI | PP/Liz/$_2$/Arg/$_2$ | C$_{58}$H$_{90}$N$_{16}$O$_{12}$ | 1203,4 | 57,84 | 57,89 | 7,48 | 7,53 | 18,61 | 18,58 |
| XXII | PP/LizOH/$_2$/Arg/$_2$ | C$_{58}$H$_{90}$N$_{16}$O$_{14}$ | 1235,4 | 56,34 | 56,23 | 7,28 | 7,19 | 18,13 | 18,04 |
| XXIII | PP/His/$_2$/Arg/$_2$ | C$_{58}$H$_{82}$N$_{18}$O$_{12}$ | 1221,3 | 56,99 | 56,89 | 6,71 | 6,67 | 20,63 | 20,52 |
| XXIV | PP/Asn/$_2$/Arg/$_2$ | C$_{54}$H$_{78}$N$_{16}$O$_{14}$ | 1175 | 55,14 | 55,19 | 6,64 | 6,68 | 19,06 | 18,98 |
| XXV | PP/Gln/$_2$/Arg/$_2$ | C$_{56}$H$_{84}$N$_{16}$O$_{14}$ | 1203,3 | 55,85 | 55,77 | 6,98 | 6,81 | 18,62 | 18,71 |

We claim:

1. A complex salt of formula 1, in which $R^1$ and $R^2$ are each selected from the group consisting of —CH=CH$_2$, —CHOH—CH$_3$ and —CHOR$^3$—CH$_3$, where $R^3$ denotes a group forming an oligomer containing ethereal and/or ester bonds, with said oligomer forming group comprising from 1 to 5 units derived from a monomer of formula 2 or where $R^1$ and $R^2$ are identical and signify a —CHR$^4$—CH$_3$ group where $R^4$ is selected from carboxymethylamino, 1-carboxyethylamino, 1-carboxy-2-methyl-propylamino, 1-carboxy-3-methyl-butylamino, 1-carboxy-2-methyl-butylamino, 1-carboxybutylamino, 1-carboxy-pentylamino, 1-carboxy-2-hydroxyethylamino, 1-carboxy-2-hydroxypropylamino, 1-carboxy-2-mercapto-ethylamino, 1-carboxy-3-methyl-thiopropylamino, 1,2-dicarboxy-ethylamino, 1-carboxy-2-carbamoyl-ethylamino, 1,3-dicarboxypropylamino, 1-carboxy-3-carbamoyl-propylamino, 1-carboxy-2-phenyl-ethylamino, 1-carboxy-2-4-hydroxy-phenylethylamino, 1-carboxy-2-indolyl-ethylamino, 2-carboxy-4-hydroxy-pyrrolidinyl, 1-carboxy-5-aminopentylamino, 1-carboxy-4-guanidyl-butylamino, 1-carboxy-4-hydroxy-5-amino-pentylamino, and 1-carboxy -2-1H-imidazole-ethylamino groups; wherein A denotes a basic amino acid; wherein m is 2–6; and wherein n is 1–5.

2. Salt according to claim 1, wherein A denotes arginine, lysine, histidine or hydroxylysine.

3. Salt according to claim 1, wherein $R^1$ and $R^2$ are identical and represent the —CHR$^4$—CH$_3$ group.

4. A mixture of complex salts containing a plurality of complex salts of formula 1 in which $R^1$ and $R^2$ are each selected from the group consisting of —CH=CH$_2$, —CHOH—CH$_3$ and CHOR$^3$—CH$_3$ where $R^3$ denotes a group forming an oligomer containing ethereal and/or ester bonds, with said oligomer forming group comprising from 1 to 5 units derived from a monomer of formula 2 or where $R^1$ and $R^2$ are identical and signify a-CHR$^4$—CH$_3$ group where $R^4$ is selected from carboxymethylamino, 1-carboxyethylamino, 1-carboxy-2-methylpropylamino, 1-carboxy-3-methyl-butylamino, 1-carboxy-2-methylbutylamino, 1-carboxybutylamino, 1-carboxy-pentylamino, 1-carboxy-2-hydroxyethylamino, 1-carboxy-2-hydro-xypropylamino, 1-carboxy-2-mercapto-ethylamino, 1-carboxy-3-methylthiopropylamino, 1,2-dicarboxy-ethylamino, 1-carboxy-2-carbamoyl-ethylamino, 1,3-dicarboxypropylamino, 1-carboxy-3-carbamoylpropylamino, 1-carboxy-2-phenyl-ethylamino, 1-carboxy-2-4-hydroxy-phenyl-ethylamino, 1-carboxy-2-indolyl-ethylamino, 2-carboxy-pyrrolidinyl, 2-carboxy-4-hydroxy-pyrrolidinyl, 1-carboxy-5-aminopentylamino, 1-carboxy-4-guanidyl-butylamino, 1-carboxy-4-hydroxy-5-amino-pentylamino, and 1-carboxy-2-1-H-imidazoleethylamino groups; wherein A denotes a basic amino acid; wherein m is 2–6; and wherein n is 1–5.

5. A mixture according to claim 4 containing amino acid salts of one or more compounds selected from the group consisting of hematoporphyrin, protoporphyrin, vinylodeuteroporphyrin and dihematoporphyrin ether.

6. A diagnostic composition containing a salt of formula 1 or a mixture of a plurality of salts of formula 1, in which $R^1$ and $R^2$ are each selected from the group consisting of —CH=CH$_2$, —CHOH—CH$_3$ and —CHOR$^3$—CH$_3$ where $R^3$ denotes a group forming an oligomer containing ethereal and/or ester bonds, with said oligomer forming group comprising from 1 to 5 units derived from a monomer of formula 2 or where $R^1$ and $R^2$ are identical and signify a—CHR$^4$—CH$_3$ group where $R^4$ is selected from carboxymethylamino, 1-carboxyethylamino, 1-carboxy-2-methyl-propylamino, 1-carboxy-3-methyl-butylamino, 1-carboxy-2-methyl-butylamino, 1-carboxybutylamino, 1-carboxy-pentylamino, 1-carboxy-2-hydroxyethylamino, 1-carboxy-2-hydro-xypropylamino, 1-carboxy-2-mercaptoethylamino, 1-carboxy-3-methyl-thiopropylamino, 1,2-dicarboxy-ethylamino, 1-carboxy-2-carbamoyl-ethylamino, 1,3-dicarboxypropylamino, 1-carboxy-3-carbamoylpropylamino, 1-carboxy-2-phenyl-ethylamino, 1-carboxy-2-4-hydroxy-phenyle-thylamino, 1-carboxy-2-indolyl-ethylamino, 2-carboxypyrrolidinyl, 2-carboxy-4-hydroxy-pyrrolidinyl, 1-carboxy-5-aminopentylamino, 1-carboxy-4-guanidyl-butylamino, 1-carboxy-4-hydroxy-5-amino-pentylamino, and 1-carboxy-2-1-H-imidazole-ethylamino groups; wherein A denotes a basic amino acid; wherein m is 2–6; wherein n is 1–5; wherein said salt or salts are present in said agent in an amount effective to detect neoplastic cells in a mammal and wherein the composition further comprises a pharmaceutically acceptable diluent or carrier.

7. A diagnostic composition according to claim 6, wherein the salt of formula 1 or the mixture of salts of formula 1 is in solid form.

8. A sterile tight container containing a salt of formula 1 or a mixture of a plurality of salts of formula 1 in solid form.

9. A salt according to claim 1 wherein the basic amino acid contains amino groups and wherein the salt is formed by reacting a hematoporphyrin or hematoporphyrin derivative containing carboxy groups with the basic amino acid containing the amino groups such that the carboxy groups and the amino groups form ionic bonds according to the equation:

$$-COOH + H_2N\text{-}R \rightarrow -COO^- + {}^+H_3N\text{-}R.$$

10. A mixture as claimed in claim 4 wherein the basic amino acid contains amino groups and wherein the plurality of complex salts is formed by reacting a hematoporphyrin or hematoporphyrin derivative containing carboxy groups with the basic amino acid containing the amino groups such that the carboxy groups and the amino groups form ionic bonds according to the equation:

$$-COOH + H_2N\text{-}R \rightarrow -COO^- + H_3N\text{-}R.$$

11. A diagnostic composition as claimed in claim 6 wherein the basic amino acid contains amino groups and wherein the salt or plurality of salts is formed by reacting a hematoporphyrin or hematoporphyrin derivative containing carboxy groups with the basic amino acid containing the amino groups such that the carboxy groups and the amino groups form ionic bonds according to the equation:

$$-COOH + H_2N\text{-}R \rightarrow -COO^- + {}^-H_3N\text{-}R.$$

12. A diagnostic composition as claimed in claim 11, wherein the neoplastic cells are selected from the group consisting of larynx cancer cells, cervix uteri cancer cells and cavity cancer cells, breast cancel cells, Burkitt lymphadenoma cells, mammary gland cancer cells and embryo kidney cancer cells.

13. A diagnostic composition as claimed in claim 11, wherein the neoplastic cells are mammary gland cancer cells.

* * * * *